United States Patent
Mai et al.

(10) Patent No.: US 10,006,856 B2
(45) Date of Patent: Jun. 26, 2018

(54) DEVICE AND METHOD FOR CALIBRATING A SCATTERED-LIGHT METER

(71) Applicant: Robert Bosch GmbH, Stuttgart (DE)

(72) Inventors: Hans Mai, Goeppingen (DE); Karl Stengel, Deizisau (DE); Christof Kaerner, Albershausen (DE); Gerhard Haaga, Ohmden (DE); Michael Neuendorf, Plochingen (DE); Peter Ostertag, Stuttgart (DE)

(73) Assignee: ROBERT BOSCH GMBH, Stuttgart (DE)

( * ) Notice: Subject to any disclaimer, the term of this patent is extended or adjusted under 35 U.S.C. 154(b) by 0 days. days.

(21) Appl. No.: 15/318,413

(22) PCT Filed: Apr. 24, 2015

(86) PCT No.: PCT/EP2015/058883
§ 371 (c)(1),
(2) Date: Dec. 13, 2016

(87) PCT Pub. No.: WO2015/197227
PCT Pub. Date: Dec. 30, 2015

(65) Prior Publication Data
US 2017/0122865 A1 May 4, 2017

(30) Foreign Application Priority Data
Jun. 23, 2014 (DE) .......... 10 2014 212 015

(51) Int. Cl.
*G01N 21/00* (2006.01)
*G01N 21/47* (2006.01)
*G01N 21/53* (2006.01)

(52) U.S. Cl.
CPC ......... *G01N 21/4785* (2013.01); *G01N 21/53* (2013.01)

(58) Field of Classification Search
CPC ................. G01N 21/4785; G01N 21/53
See application file for complete search history.

(56) References Cited

U.S. PATENT DOCUMENTS

2013/0057860 A1\* 3/2013 Sieg .......... G01N 21/4785
356/341

FOREIGN PATENT DOCUMENTS

| DE | 102010002423 A1 | 9/2011 |
| DE | 102012200739 A1 | 7/2013 |
| DE | 102012104721 A1 | 12/2013 |
| EP | 2600139 A1 | 6/2013 |

OTHER PUBLICATIONS

International Search Reported dated Aug. 6, 2015, of the corresponding International Application PCT/EP2015/058883 filed Apr. 24, 2015.

\* cited by examiner

*Primary Examiner* — Michael P Stafira
(74) *Attorney, Agent, or Firm* — Norton Rose Fulbright US LLP; Gerard Messina

(57) ABSTRACT

A calibration device for calibrating a scattered-light meter, which is developed for measuring a particle concentration, in particular in automotive exhaust gases, has at least one diffuser which emits scattered light of an intensity and distribution defined by the diffuser when irradiated by light. In addition, the calibration device has a calibration-light source, which is situated within the diffuser or on an external surface of the diffuser.

13 Claims, 2 Drawing Sheets

DEVICE AND METHOD FOR CALIBRATING A SCATTERED-LIGHT METER

FIELD

The present invention relates to a device and a method for calibrating a scattered-light meter as it is used for measuring particle concentrations in automotive exhaust gases.

BACKGROUND INFORMATION

Conventionally, scattered-light methods are used for measuring the concentration of particles in exhaust gases and other colloids.

A measuring device provided for such a purpose usually includes a high-power light source such as a laser, which radiates light into a measuring chamber through which the colloid to be measured is routed. At least one light sensor, which detects light that has been scattered by particles present in the colloid, is allocated to the measuring chamber. In order to check the proper functioning of such a measuring device and to calibrate the measuring device, it is necessary to adjust a defined state in the measuring chamber in which the irradiated light is scattered in a defined and known manner. Measuring devices that are used for official measurements are subject to an obligatory calibration which further increases the need for supplying precise measuring results with high reliability. Such a measuring device in described in German Patent Application No. 10 2010 002423.6.

SUMMARY

It is an object of the present invention to provide a device that makes it possible to check and calibrate a scattered-light meter in a simple, reliable and precise manner.

This objective may be achieved by a calibration device according to the present invention, and by a method according to the present invention.

A calibration device according to the present invention for calibrating a scattered-light meter, which is designed to measure a particle concentration in automotive exhaust gases, has at least one diffuser which emits scattered light of an intensity and distribution defined by the diffuser in response to light irradiation. A calibration light source is situated in the diffuser.

The use of a diffuser provided with a calibration light source makes it easy and fast to generate scattered light in the measuring chamber. In comparison with the use of a calibration gas or conventional calibration devices that have reflective planes, for instance, such a diffuser is easier to handle and can be manufactured more easily with reproducible characteristics and the required precision. In addition, such a diffuser is subject neither to consumption nor wear during the calibration.

A particle concentration hereinafter also refers to quantities that correspond to a particle concentration, such as a turbidity value, a mass concentration or a number concentration.

The present invention also includes a method for calibrating a scattered-light meter for measuring the particle concentration in automotive exhaust gases, having a scattered-light measuring chamber, at least one light source and at least one scattered-light sensor; the method includes the introduction of a calibration device according to the present invention into the scattered-light measuring chamber in a defined position; the switching on of a calibration light source of the diffuser; the recording of light (scattered light) scattered by the diffuser with the aid of the light sensor; and the outputting of a measuring signal and the comparing of the output measuring signal to a predefined reference value.

In comparison to calibration devices without a calibration light source, the device according to the present invention and the method according to the present invention make it possible to reduce the influence of reflections at the entry points and exit points of the diffuser. Reflections at the entry points and exit points of the diffuser have an effect on the absolute value of the power recorded by the light sensors and thus affect the measured values.

Because of the calibration light source in the diffuser, which is able to be connected and disconnected in a flexible manner, a significantly more precise measurement and thus adjustment of the scattered-light meter is possible by calculating the difference of the receiver signals in the activated and deactivated state of the calibration light source.

The method according to the present invention has the following method steps:

a) Illuminating the calibration device with light from the light source;

b) Recording the light scattered by the calibration device using the at least one light sensor, and outputting a first signal;

c) Switching on the calibration light source, while the calibration device continues to be illuminated by light from the light source;

d) Recording the light scattered by the calibration device using the at least one light sensor, and outputting a measuring signal;

e) Comparing the difference of the first signal and the measuring signal to a predefined reference value.

Such a method makes it possible to calibrate a scattered-light meter with high precision in an especially simple and reliable manner. In particular, no special calibration gases are necessary, which are difficult to store and handle and in which the particle concentration depends on external parameters such as the pressure and/or the temperature.

The calibration light source may be situated within the diffuser or on an external surface of the diffuser. Because of the flexible design, it is possible to specify a radiation of the scattered-light meter in defined directions as a function of the design of the scattered-light meter.

In one further specific embodiment, the calibration light source is able to emit light having a defined intensity and/or power, which is adjustable via at least one current-measuring point. This allows for a calibration of the light sensors in a broad power spectrum. Without a calibration light source, a different diffuser with a different number and distribution of scattering centers would have to be used in the scattered-light meter for the representation of different particle concentrations in each case. By varying the intensity and the power of the calibration light source, it is possible to represent different particle concentrations using the same diffuser, without exchanging the diffuser.

The placement of at least one diaphragm element having at least one aperture on at least one exterior surface of the diffuser is advantageous since the radiation of the light emitted by the diffuser is thereby able to be directed in a defined manner in one direction.

A further advantage results if the diffuser is developed in such a way that scattered light and/or light of the calibration light source is emitted via at least two external surfaces in different directions in space. This allows for an arbitrary placement of the light sensors around the diffuser.

The diffuser may exhibit the defined scatter behavior either as a result of an appropriate design of the external surfaces or on account of a predefined number and/or placement of scatter centers. The use of scattering centers is the easiest way to represent the scatter behavior of a particle concentration in the scattered-light meter.

The present invention also includes the use of a diffuser which emits scattered light of a predefined intensity and distribution in response to a defined irradiation from a light source for the calibration of a scattered-light meter designed for measuring a particle concentration in automotive exhaust gases or in other colloids. A calibration light source, which emits light having a defined intensity and/or power, is situated within the diffuser or on an external surface of the diffuser.

Exemplary embodiments of the present invention are described below on the basis of the figures.

DETAILED DESCRIPTION OF EXAMPLE EMBODIMENTS

Figure 1:
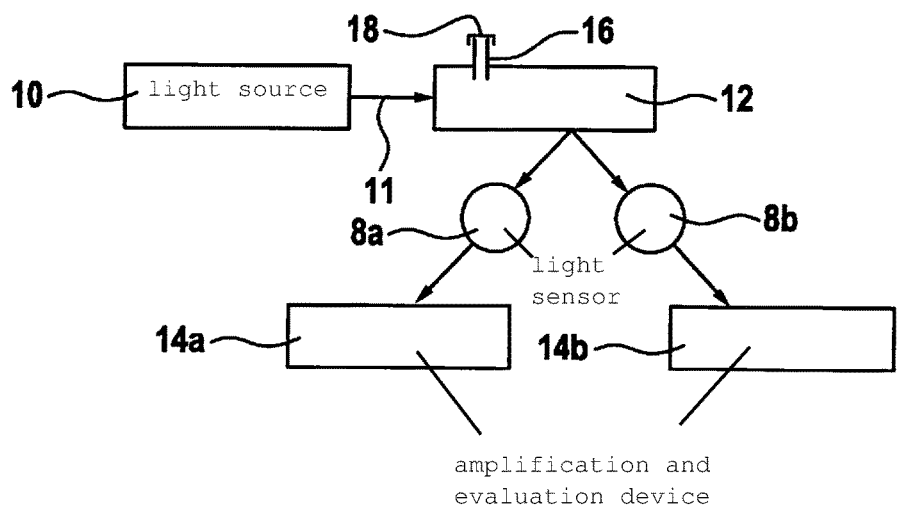
FIG. 1 shows schematically, the structure of a scattered-light meter.

FIG. 1 schematically shows the structure of a scattered-light meter for measuring a particle concentration in automotive exhaust gases or in other colloids.

Such a scattered-light meter includes a scattered-light measuring chamber 12 through which exhaust gas from a motor vehicle is guided with the aid of feed and discharge lines that are not shown in FIG. 1. The exhaust gas may be guided through scattered-light measuring chamber 12 by pressure generated by the engine of the motor vehicle, also known as exhaust backpressure. Optionally, a pump (not shown in FIG. 1) may be provided in addition in order to boost the exhaust-gas flow through scattered-light measuring chamber 12.

The scattered-light meter has at least one light source 10 which, for instance, is developed as a laser. In the switched-on state, light source 10 produces a beam of light 11 having a defined intensity and direction within scattered-light measuring chamber 12.

In addition, at least one light sensor 8a, 8b is provided in scattered-light measuring chamber 12; in the exemplary embodiment shown in FIG. 1, two light sensors 8a, 8b are present. They detect light from light source 10 that has been scattered by particles which are present in the exhaust-gas flow guided through scattered-light measuring chamber 12. In the schematic illustration of FIG. 1, light source 10 and light sensors 8a, 8b are shown outside scattered-light measuring chamber 12 for better clarity, although in reality, they are at least partially situated within or directly at scattered-light measuring chamber 12.

Preferably, light sensors 8a, 8b are situated at different angles in relation to the direction of irradiated beam of light 11 so that they detect scattered light 20 scattered at different angles. The electrical signals output by scattered-light sensors 8a, 8b, are forwarded to one or more electronic amplification and evaluation device(s) 14a, 14b, which evaluate the signals and ascertain and output the concentration of particles in the gas flow guided through measuring chamber 12.

In order to obtain highly precise measuring results that comply with high legal requirements, for example, a scattered-light meter must be calibrated on a regular basis. For this purpose, scattered light that corresponds to a predefined, known particle concentration is generated in scattered-light measuring chamber 12, and evaluation devices 14a, 14b are adjusted in such a way that they output the specified, known particle concentration as the result of the measurement.

According to the present invention, scattered-light measuring chamber 12 includes at least one receiving device 16 for accommodating a calibration device 1 according to the present invention. In the exemplary embodiment shown, receiving device 16 is developed as an opening, through which a calibration device 1 according to the present invention and as described in the following text can be inserted into scattered-light measuring chamber 12.

If no calibration device 1 is inserted into scattered-light measuring chamber 12, the opening of receiving device 16 is sealed by a lid 18 in order to prevent the entry of particles and/or light from the environment into scattered-light measuring chamber 12 and a thereby induced falsification of the measuring results.

In one alternative exemplary embodiment, which is not shown, calibration device 1 may be inserted into scattered-light measuring chamber 12 through one of the openings (not shown in FIG. 1) provided for the supply and discharge of the automotive exhaust gases. This is possible because no exhaust gases are guided through scattered-light measuring chamber 12 during the calibration process.

Figure 2:
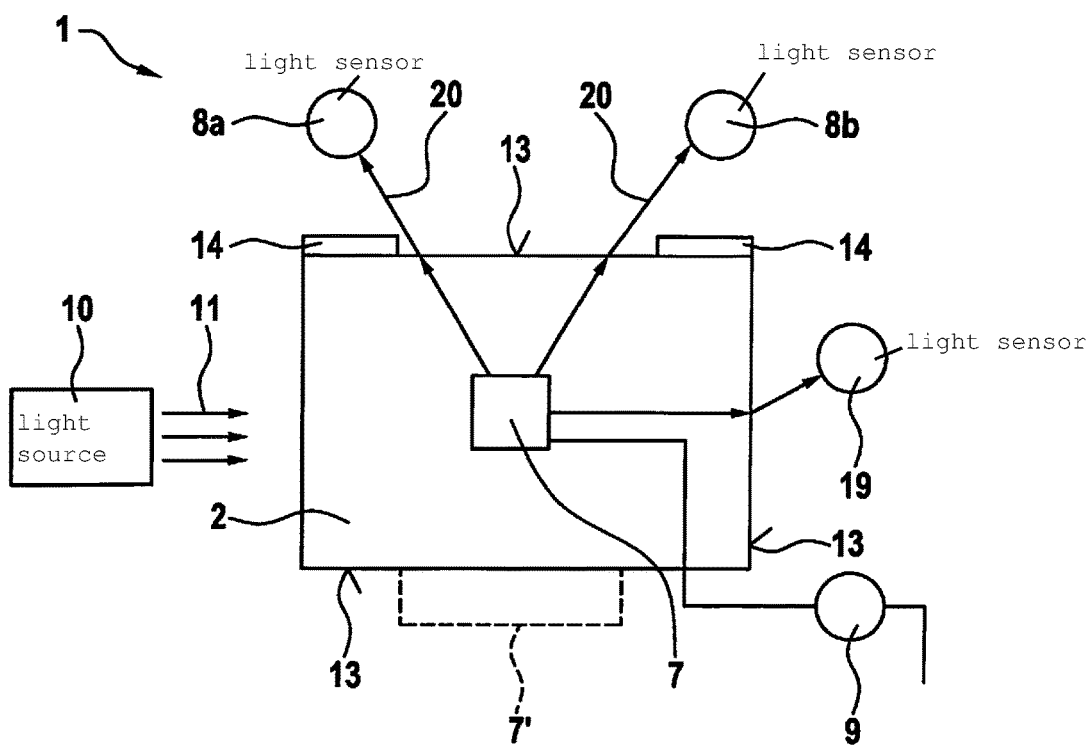
FIG. 2 shows schematically, the structure of a calibration device according to the present invention according to a first exemplary embodiment.

FIG. 2 shows the structure of a calibration device 1 according to the present invention in a schematic illustration.

A calibration device 1 according to the present invention includes a diffuser 2. Diffuser 2 has a transparent carrier material which preferably is a material featuring an especially low thermal expansion, such as a glass-ceramics material.

Figure 3:
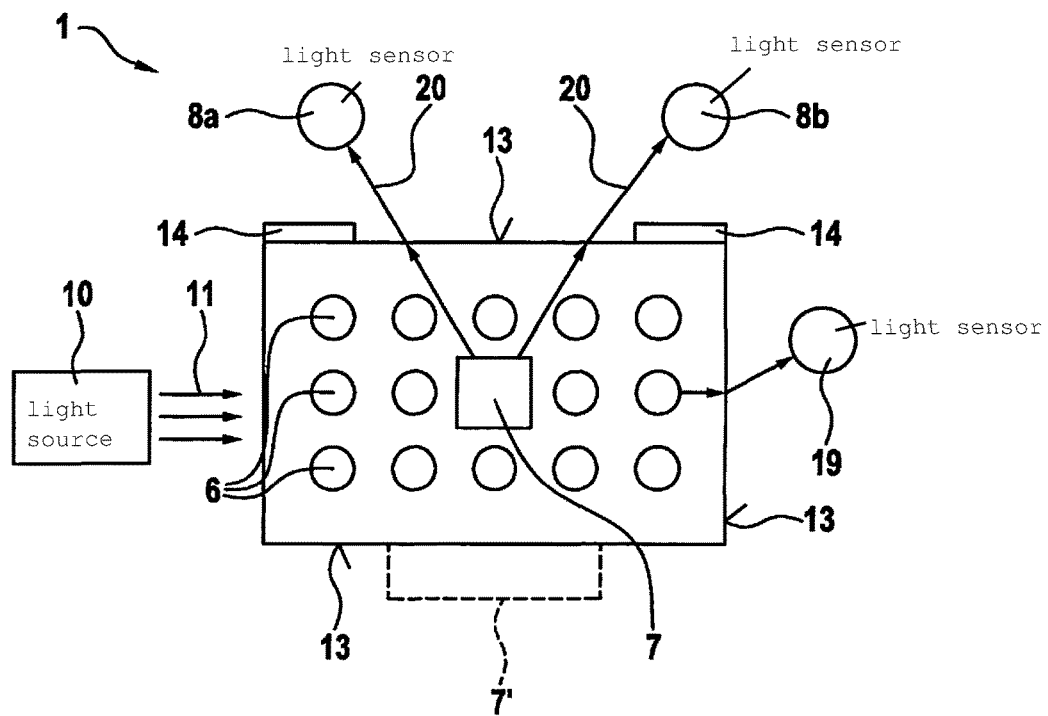
FIG. 3 shows schematically, the structure and the function principle of a diffuser according to a second exemplary embodiment.

Diffuser 2 may have arbitrary geometrical dimensions. The geometry of diffuser 2 is preferably adapted to the dimensions of scattered-light measuring chamber 12. A diffuser 2 having a cuboid volume, which is shown in cross-section, is depicted in FIGS. 2 and 3 by way of example.

Calibration device 1 includes a calibration light source 7 situated within diffuser 2. In an alternative exemplary embodiment, calibration light source 7' is disposed on an external surface 13 of diffuser 2. This exemplary embodiment is shown in FIG. 2 and FIG. 3 with the aid of dashed lines. In alternative exemplary embodiment 7', calibration-light source 7' emits light radiation in the direction of diffuser 2 so that the light passes through diffuser 2 before it leaves diffuser 2 again at one or more external surface(s) 13.

Calibration-light source 7, 7' may be switched on and off as desired. Calibration-light source 7, 7' is able to emit light of a defined intensity and/or power.

Calibration-light source 7, 7' is preferably developed as an LED. An LED is able to be controlled in its light output over multiple decades by adjusting a current. The supplied current is able to be regulated with the aid of a current-measuring point 9 so that calibration-light source 7, 7' emits light of a reproducible intensity in the direction of light sensors 8a, 8b.

FIG. 3 shows an alternative specific embodiment of a diffuser 2, in which a number of scattering centers 6 are disposed. These scattering centers 6 preferably have a defined size and a defined spacing between one another. Scattering centers 6 are preferably situated in a regular grid pattern within diffuser 2, as schematically illustrated in FIG. 3. Scattering centers 6 may be crystallites formed in diffuser 2.

A diffuser 2 designed in this manner has defined scattering characteristics that remain constant over a long period of time and which correspond to the scattering characteristics of a specific particle concentration. When irradiated by light 11 from light source 10, diffuser 2 emits scattered light 20 that has a defined intensity and spatial distribution. Scattered light 20 generated by diffuser 2 impinges upon scattered-light sensors 8a and 8b and is detected by the sensors, as schematically illustrated in FIG. 3.

In one alternative exemplary embodiment, calibration device 1 has a diaphragm element 14 including at least one diaphragm aperture on at least one external surface 13 of diffuser 2. This diaphragm element 14 may be situated on one or more external surface(s) of diffuser 2 with or without scattering centers 6.

In exemplary embodiments, diffuser 2 may be developed in such a way that scattered light 20, 20' from light source 10 and/or the light from calibration-light source 7,7' is emitted via at least two external surfaces 13 in different spatial directions.

To carry out a calibration according to the present invention, a calibration device 1 according to the invention, which has a diffuser 2 as shown in FIG. 2 or FIG. 3, is brought into a defined position within measuring chamber 12 through the opening of receiving device 16. Calibration-light source 7,7' is switched on so that calibration-light source 7,7' generates light of a specified intensity. Depending on the specific embodiment of diffuser 2, this light is scattered with a defined, specified spatial intensity distribution, detected by scattered-light sensors 8a, 8b and converted into electrical signals. The electrical signals are converted into a particle concentration by one or more evaluation device(s) 14a, 14b.

The particle concentration ascertained by evaluation devices 14a, 14b is compared to a defined particle concentration that is allocated to the respective intensity of calibration-light source 7,7'. If the particle concentration ascertained by evaluation devices 14a, 14b deviates from the specified particle concentration allocated to diffuser 2, then evaluation devices 14a, 14b are readjusted until the particle concentration ascertained by evaluation devices 14a, 14b corresponds to the specified particle concentration allocated to the intensity of calibration-light source 7,7' within the specified precision.

The comparing of the calculated particle concentration to the specified particle concentration and the adjustment of evaluation devices 14a, 14b may take place automatically or manually.

To carry out a further calibration according to the present invention, a calibration device 1 according to the invention, which has a diffuser 2 as shown in FIG. 2 or 3, is brought into a defined position within measuring chamber 12 through the opening of receiving device 16. In the process, calibration device 1 is illuminated by light 11 from light source 10. Light 11 is scattered by diffuser 11 and scattered light 20 is recorded by calibration device 1 having the at least one light sensor 8a, 8b and allocated to a first signal, which is output.

During the illumination of diffuser 2 by light from light source 10, calibration-light source 7,7' is then switched on so that calibration-light source 7,7' generates light of a specified intensity. The light of light source 10 and of calibration-light source 7,7' superposes and is scattered at diffuser 2 prior to being detected by scattered-light sensors 8a, 8b and converted into a measuring signal, which is output.

In a further step, the difference is formed of the first signal and the measuring signal. The difference of the first signal and the measuring signal ascertained by evaluation devices 14a, 14b is compared to a defined particle concentration allocated to the respective intensity of calibration-light source 7,7'. If the particle concentration ascertained by evaluation devices 14a, 14b deviates from the specified particle concentration allocated to diffuser 2, then evaluation devices 14a, 14b will be readjusted until the particle concentration ascertained by evaluation devices 14a, 14b corresponds to the specified particle concentration allocated to the intensity of calibration-light source 7,7' within the specified accuracy.

By varying the intensity of calibration-light source 7,7', the scattering behavior of diffuser 2 can be adapted to the scattering behavior of exhaust gases having different particle concentrations and the calibration of the scattered-light meter is able to be carried out in a simple manner at different operating points. This makes it possible to achieve a particularly precise calibration of the scattered-light meter across a wide measuring range.

What is claimed is:

1. A calibration device for calibrating a scattered-light meter that is designed for measuring a particle concentration in automotive exhaust gases, the calibration device comprising:
    at least one diffuser which emits scattered light of an intensity and distribution defined by the diffuser when irradiated by light; and
    a calibration-light source to emit the light,
    wherein the calibration-light source is situated one of: i) within the diffuser, or ii) on an external surface of the diffuser.

2. The calibration device as recited in claim 1, wherein the calibration-light source is able to be switched on and off.

3. A calibration device for calibrating a scattered-light meter that is designed for measuring a particle concentration in automotive exhaust gases, the calibration device comprising:
    at least one diffuser which emits scattered light of an intensity and distribution defined by the diffuser when irradiated by light; and
    a calibration-light source to emit the light,
    wherein the calibration-light source emits light of at least one of defined intensity and defined power, and is adjustable via at least one current-measuring point.

4. A calibration device for calibrating a scattered-light meter that is designed for measuring a particle concentration in automotive exhaust gases, the calibration device comprising:
    at least one diffuser which emits scattered light of an intensity and distribution defined by the diffuser when irradiated by light;
    a calibration-light source to emit the light; and
    a diaphragm element having at least one aperture allocated to at least one external surface of the diffuser.

5. The calibration device as recited in claim 1, wherein the diffuser is designed in such a way that at least one of scattered light and light of the calibration-light source, is emitted via at least two external surfaces in different spatial directions.

6. The calibration device as recited in claim 1, wherein the diffuser has a number of scattering centers.

7. A method for calibrating a scattered-light meter, which is designed for measuring the particle concentration in automotive exhaust gases, and which includes a scattered-light measuring chamber, at least one light source, at least one scattered-light sensor, and a calibration device placed into the scattered-light measuring chamber in a defined position, the method comprising:
- 1) switching on a calibration-light source of the calibration device, the calibration-light source being situated one of: within a diffuser, or on an external surface of the diffuser;
- 2) recording light scattered by the calibration device as a result of switching on the calibration-light source with the aid of the at least one light sensor, and outputting a measuring signal; and
- 3) comparing the measuring signal to a specified reference value.

8. The method as recited in claim 7, wherein the following steps a) through b) are carried out prior to step 1):
- a) illuminating the calibration device by light from the light source; and
- b) recording the light scattered by the calibration device with the aid of the at least one light sensor and outputting a first signal;
- wherein the steps 1) and 2) are executed while the calibration device is illuminated by light from the light source, and the difference of the first signal and the measuring signal is compared to the specified reference value in step 3).

9. A method, comprising:
using a diffuser which, in response to a defined irradiation by light from a light source, emits scattered light having a specified intensity and distribution for the calibration of a scattered-light meter which is developed for measuring a particle concentration in automotive exhaust gases or in other colloids, a calibration-light source which emits light of at least one of a defined intensity and a defined power being situated one of within the diffuser or on an external surface of the diffuser.

10. The method as recited in claim 9, wherein the calibration-light source is adjustable via at least one current-measuring point.

11. The method as recited in claim 9, wherein a diaphragm element having at least one aperture is allocated to at least one external surface of the diffuser.

12. The method as recited in claim 7, wherein the calibration-light source emits light of at least one of defined intensity and defined power, and is adjustable via at least one current-measuring point.

13. The method as recited in claim 7, wherein a diaphragm element having at least one aperture is allocated to at least one external surface of the diffuser.

\* \* \* \* \*